(12) United States Patent
Sasady (10) Patent No.: US 9,179,891 B2
(45) Date of Patent: Nov. 10, 2015

(54) ULTRASOUND PROBE

(75) Inventor: Niels-Christian Lendrick Sasady, Frederiksberg (DK)

(73) Assignee: B-K Medicals Aps, Herlev (DK)

( * ) Notice: Subject to any disclaimer, the term of this patent is extended or adjusted under 35 U.S.C. 154(b) by 377 days.

(21) Appl. No.: 13/496,298

(22) PCT Filed: Sep. 18, 2009

(86) PCT No.: PCT/IB2009/007090
§ 371 (c)(1),
(2), (4) Date: Mar. 15, 2012

(87) PCT Pub. No.: WO2011/033333
PCT Pub. Date: Mar. 24, 2011

(65) Prior Publication Data
US 2012/0174675 A1    Jul. 12, 2012

(51) Int. Cl.
*G01D 21/00* (2006.01)
*A61B 1/32* (2006.01)
(Continued)

(52) U.S. Cl.
CPC .............. *A61B 8/4488* (2013.01); *A61B 1/303* (2013.01); *A61B 1/32* (2013.01); *A61B 8/12* (2013.01); *A61B 8/4209* (2013.01); *A61B 8/4472* (2013.01)

(58) Field of Classification Search
CPC ......... G01N 29/265; G01H 1/00; G01H 1/08; G01H 1/003; G01H 1/006; G01P 15/093; G01D 11/30; G01D 11/245; G01F 1/3209; G01F 1/3254; A61B 1/32; A61B 1/06; A61B 1/015; A61B 1/303; A61B 17/0206; A61B 17/42; A61B 1/12

USPC ......... 73/661, 649, 653, 655, 866.5; 600/202, 600/213, 215, 220, 221, 223, 226, 437, 446, 600/462, 463
See application file for complete search history.

(56) References Cited

U.S. PATENT DOCUMENTS 2,579,849 A * 12/1951 Newman ........................ 600/215
2,672,859 A *  3/1954 Jones ............................. 600/205
(Continued)

FOREIGN PATENT DOCUMENTS

WO    WO 2005/058128    *  6/2005
WO    WO 2009/040738    *  4/2009

OTHER PUBLICATIONS

International search report for PCT/IB2009/007090 published as WO 2011/033333, dated Feb. 22, 2010.

*Primary Examiner* — Helen Kwok
(74) *Attorney, Agent, or Firm* — Anthony M. Del Zoppo, III; Driggs, Hogg, Daugherty & Del Zoppo, Co., LPA (57) ABSTRACT

An ultrasound probe (100) includes an elongate handle (102) with first and second end regions (101, 103). The probe (100) further includes first and second blade sections (104, 112). The first blade section (104) is attached to the first end region (101) and extends in a direction away from the first end region. The second blade section (112) is movably attached to the first end region (101) and extends in the same direction as the first blade section (104). The second blade section (112) is configured to move between a first position in which the second blade section (112) is next to the first blade section (104) and a second position in which the second blade section (112) is further away from the first blade section (104). The probe (100) further includes transducer array (110) affixed to the first blade section (104) opposite the first end region (101) and in between the first and second blade sections (102, 104).

22 Claims, 6 Drawing Sheets

(51) Int. Cl.
*A61B 1/12* (2006.01)
*A61B 8/00* (2006.01)
*A61B 1/303* (2006.01)
*A61B 8/12* (2006.01)

(56) References Cited

U.S. PATENT DOCUMENTS

| | | | |
|---|---|---|---|
| 3,716,047 A * | 2/1973 | Moore et al. | 600/212 |
| 4,884,559 A * | 12/1989 | Collins | 600/205 |
| 4,971,036 A * | 11/1990 | Collins | 600/202 |
| 5,143,054 A * | 9/1992 | Adair | 600/104 |
| 5,368,598 A * | 11/1994 | Hasson | 606/119 |
| 5,499,964 A * | 3/1996 | Beck et al. | 600/220 |
| 5,868,668 A * | 2/1999 | Weiss | 600/224 |
| 5,873,820 A * | 2/1999 | Norell | 600/220 |
| 6,004,265 A * | 12/1999 | Hsu et al. | 600/223 |
| 6,210,330 B1 * | 4/2001 | Tepper | 600/439 |
| 6,379,299 B1 * | 4/2002 | Borodulin et al. | 600/220 |
| 6,569,091 B2 * | 5/2003 | Diokno et al. | 600/220 |
| 6,595,917 B2 * | 7/2003 | Nieto | 600/223 |
| 6,960,166 B1 * | 11/2005 | Wong et al. | 600/221 |
| 7,311,663 B2 * | 12/2007 | Marcotte | 600/222 |
| 8,096,945 B2 * | 1/2012 | Buchok et al. | 600/205 |
| 8,376,942 B2 * | 2/2013 | Krauter et al. | 600/222 |
| 8,388,523 B2 * | 3/2013 | Vivenzio et al. | 600/178 |
| 8,403,842 B2 * | 3/2013 | Sakhel | 600/221 |
| 8,435,175 B2 * | 5/2013 | McMahon et al. | 600/223 |
| 8,568,324 B2 * | 10/2013 | Roundhill | 600/444 |
| 2002/0133060 A1 * | 9/2002 | Doyle | 600/210 |
| 2003/0225313 A1 * | 12/2003 | Borodulin et al. | 600/135 |
| 2005/0234305 A1 * | 10/2005 | Licciardi | 600/221 |
| 2006/0149129 A1 * | 7/2006 | Watts et al. | 600/113 |
| 2008/0027423 A1 * | 1/2008 | Choi et al. | 606/40 |
| 2009/0205665 A1 * | 8/2009 | Tanaka et al. | 128/205.27 |

* cited by examiner

ULTRASOUND PROBE

RELATED APPLICATION

This application is a national filing of PCT application Serial No. PCT/IB2009/007090, filed Sep. 18, 2009, published as WO2011/033333 on Mar. 24, 2011.

TECHNICAL FIELD

The following generally relates to ultrasonography and more particularly to an ultrasound probe.

BACKGROUND

Ultrasonography is an imaging technique used to visualize subcutaneous structures in a subject, for example, an internal organ, an internal muscle structure, or a fetus within a uterus. When this technique is used for a general obstetric exam, a transducer is placed on the outside of the abdomen (e.g., transadominally) of a pregnant woman and emitted sound waves penetrate through the skin, the bladder, and other subcutaneous structures. Reflected sound waves are detected and images are created based on the reflected waves, for visualization of the uterus.

One medical technique where transabdominal ultrasonography is used is in vitro fertilization (IVF), which is a process of fertilization of an egg by a sperm that takes place outside a woman's body (e.g., in a laboratory) and then the fertilized egg is implanted in the uterus. IVF is used when there is abnormal sperm or when fallopian tubes are not patent. The process includes hormonally controlling the ovulatory process, removing ova from a woman's ovaries and letting sperm fertilize them in a fluid medium.

The fertilized egg (e.g., zygote) is then transferred to the patient's uterus with the intent to establish a successful pregnancy. A general method for transfer includes using a speculum, which allows a doctor to have limited direct vision into the vaginal cavity, and inserting a catheter through the cavity until it reaches the uterus. The zygote is then placed on the uterus wall via the catheter. A transabdominal ultrasound has been used to image the uterus to verify placement of the zygote implantation.

Unfortunately, the speculum and/or other structures between the abdomen surface and the uterus may attenuate the ultrasound beam and degrade image quality, making it more difficult to verify placement. Moreover, it may be difficult to visually determine the optimal target for embryo placement, known as the maximal potential (MP) point, from outside of the uterus.

SUMMARY

Aspects of the application address the above matters, and others.

In one aspect, an ultrasound probe includes an elongate handle with first and second end regions. The probe further includes first and second blade sections. The first blade section is attached to the first end region and extends in a direction away from the first end region. The second blade section is movably attached to the first end region and extends in the same direction as the first blade section. The second blade section is configured to move between a first position in which the second blade section is next to the first blade section and a second position in which the second blade section is further away from the first blade section. The probe further includes a transducer array affixed to the first blade section opposite the first end region and in between the first and second blade sections.

In another aspect, an ultrasound probe includes first and second blade sections, wherein the first blade section is longer than the second blade section by an offset, and a transducer array affixed to the first blade section in between the first and second blade sections and within the offset.

In another aspect, a method includes positioning an ultrasound probe within a cavity. The ultrasound probe includes an elongate handle with first and second end regions. A first blade section is attached to the first end region and extends in a direction away from the first end region. The first blade section has a first length relative to the first end region. A second blade section is movably attached to the first end region and extends in the same direction as the first blade section. The second blade section has a second length relative to the first end region and the first length is greater than the second length. The second blade section is configured to move towards and away from the first blade section. The probe further includes a transducer array affixed to the first blade section opposite to a location at which the first blade section is attached to the handle and in between the first and second blade sections.

Those skilled in the art will recognize still other aspects of the present application upon reading and understanding the attached description.

DETAILED DESCRIPTION

Figure 1:
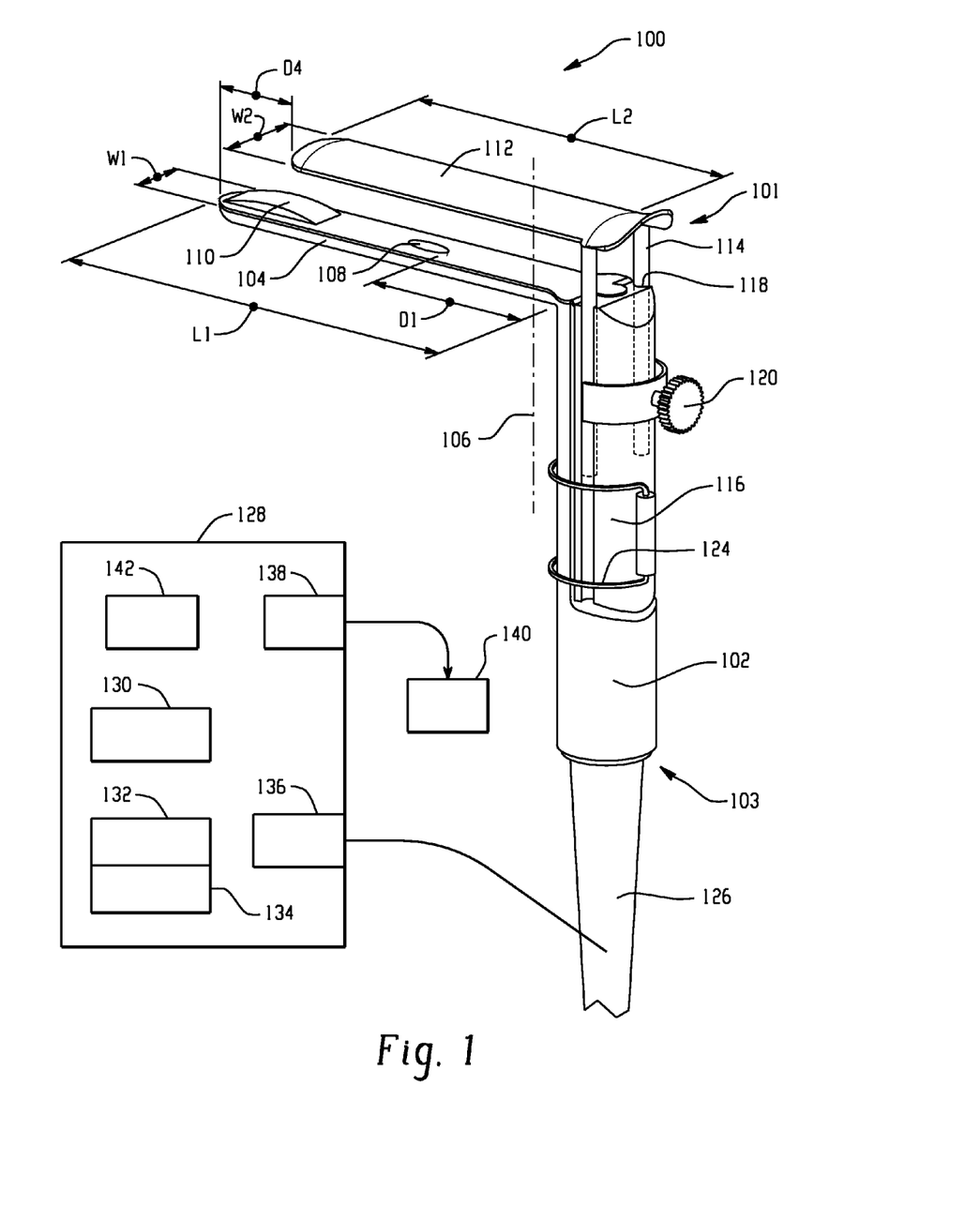
FIG. 1 illustrates a first example probe.
Figure 2:
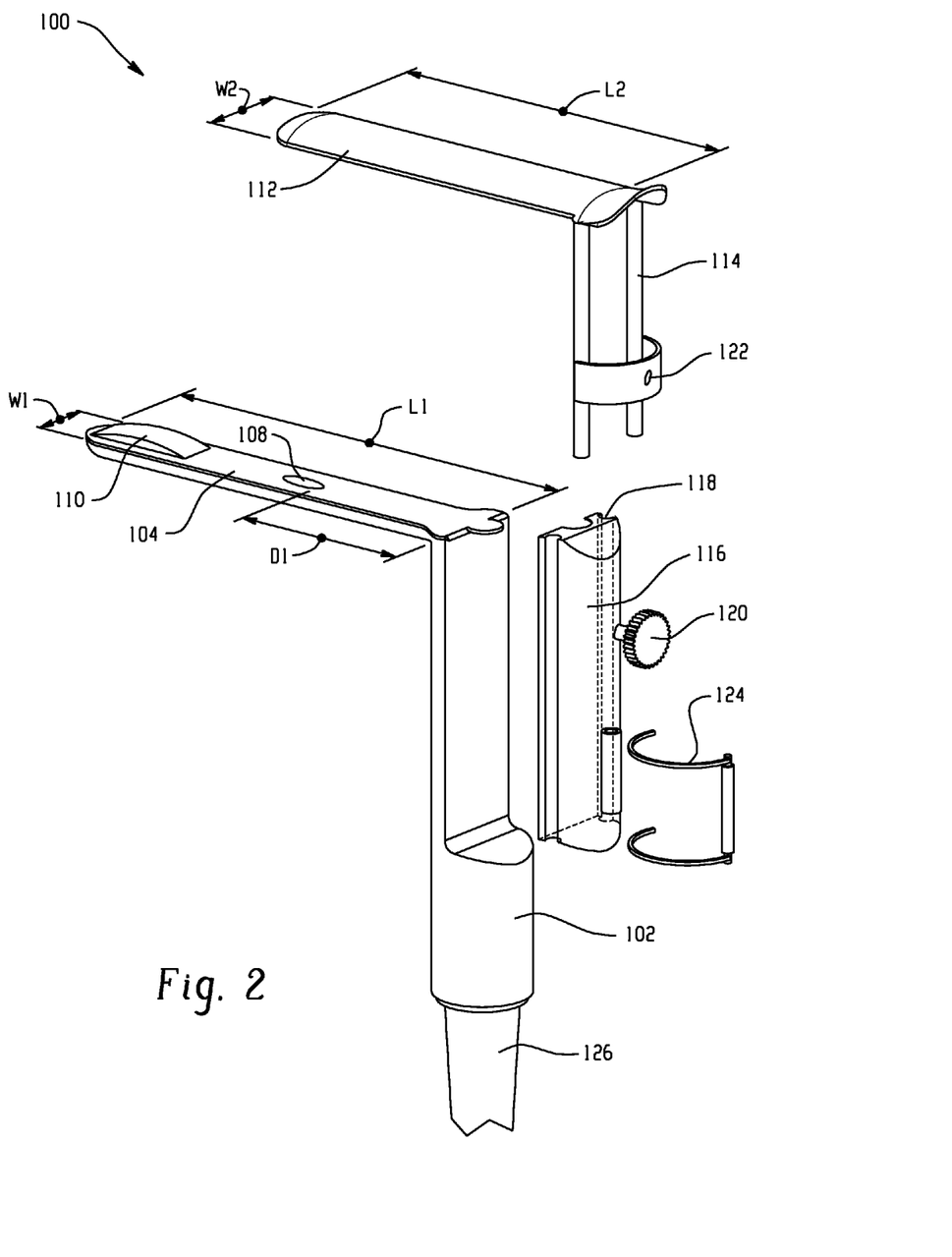
FIG. 2 illustrates a component view of the first example probe.

FIGS. 1 and 2 depict an example ultrasound probe 100. FIG. 1 illustrates an assembled probe 100, and FIG. 2 illustrates the probe 100 with several components detailed therefrom.

The probe 100 includes an elongate handle 102 having a first end region 101 and a second end region 103. The handle 102 allows a user to hold the probe 100 during a procedure. The handle 102 is composed of a sterilizable material, examples of which include stainless steel, plastic or other material.

A posterior blade section 104 attaches to the handle 102 and extends away from the handle 102 at the first end region 101. In the illustrated embodiment, the posterior blade section 104 extends substantially perpendicularly from the handle 102. In other embodiments, the posterior section 104 may be positioned between an angular range of thirty degrees (30°) and one hundred and forty degrees (140°), such as between 45° and 135°, in relation to an axis 106 running parallel to the handle 102.

The illustrated posterior blade section 104 has a width W1 within a range of about ten millimeters (10 mm) and twenty-five millimeters (25 mm), such as 16 mm to 21 mm.

The posterior section 104 has a length L1 in a range of about one hundred five millimeters (105 mm) and one hundred fifty millimeters (150 mm), such as 110 mm to 140 mm. The width W1 and length L1 may facilitate access to extended areas of a cavity (e.g., vagina, anus or throat).

The posterior section 104 is composed of a sterilizable material. Example materials include stainless steel, plastic or other material. In one instance, the material can be heated up to about one hundred thirty degrees Celsius (130° C.) or higher, such as 180° C., for sterilization.

A light source 108 is located about a center region of the posterior section 104. The illustrated light source 108 is located at about a distance D1 from the handle 102. Other distances are also contemplated. The light source 108 may be a light emitting diode (LED), a laser or other low-power light source.

A transducer array 110 is located on an end region of the posterior section 104, opposite the handle 102. The transducer 110 has a range of view, such as, for example, between 0° and 60°, but can be any between 0° and 360°. The transducer 110 is configured to emit ultrasound in a frequency range of about one megahertz (1 MHz) to about fifteen megahertz (15 MHz), such as 7.5 MHz and 12 MHz. This frequency range may allow a higher image resolution within a region of interest in relation to a configuration of the probe 100 with a lower frequency range. A higher image resolution may allow viewing on a region, which is obstructed by internal structures and/or tools.

An anterior blade section 112 is movably affixed to the handle 102. The anterior section 112 extends away from the first end region 101 of the handle 102 in substantially the same direction as the posterior section 104 and includes standoffs 114. The anterior section 112 extends from the first end region 101 by a lesser degree than the posterior section 104 by a distance D4, and is therefore longitudinally offset therefrom. Due to the offset, the anterior section 112 does not obstruct the range of view of transducer 110.

The offset is in a range from about 10 to 50 mm such as 30 to 40 mm. The anterior blade section 112 has a width W2 within a range of about ten millimeters (10 mm) and twenty-five millimeters (25 mm), such as 16 mm to 21 mm. The widths W1 and W2 may be similar or different for a particular probe 100. The anterior section 112 has a length L2 in the range of about one hundred five millimeters (105 mm) and one hundred fifty millimeters (150 mm), such as 110 mm to 140 mm.

As illustrated in FIG. 1, the anterior section 112 is located substantially parallel to posterior section 104. The anterior section 112 is also composed of a material similar to that of the posterior section 104. The anterior section 112 may be disposable or sterilizable.

A handle attachment 116 has one or more grooves or recesses 118 configured to receive the standoffs 114 of the anterior section 104. The standoffs 114 are configured to slide in the recesses 118, which moves the anterior section 112 towards and/or away from the handle attachment 116 through a plurality of positions.

In one instance, the anterior section 112 is positioned into a first position in which a surface of the anterior blade section 112 rests upon a surface of posterior blade section 104. In this position, the anterior section 112 and the posterior section 104 are substantially parallel. This position is referred to herein to as a "closed" position. In another instance, the anterior section 112 is positioned at a second substantially parallel position at which the anterior section 112 is at a predetermined distance from the posterior section 104. This position is referred to herein as an "open" position.

The illustrated handle attachment 116 is composed of a material similar to the posterior section 104 and the anterior section 112. The handle attachment 116 is also disposable or sterilizable.

A fastener 120, such as a knob, pin or other fastener, holds the anterior section 112 to the handle attachment 116, and hence to the probe 100. In one embodiment, the fastener 120 extends through an aperture 122 on the anterior blade section 112. The illustrated fastener 120 is loosened by rotating the fastener in one direction, which allows the standoffs 114 to be translated to a desired position. Positioning may occur manually, electronically or in another manner. The fastener 120 is tightened by rotating the fastener 120 in an opposite direction, which locks the standoffs 114 at its position.

An adjustable bracket 124 holds the handle attachment 116 to the handle 102. The bracket 124 is pivotally connected to the handle attachment 116 and engages the handle 102 to inhibit movement of the handle attachment 116 in relation to the handle 102. In one instance, bracket 124 secures handle attachment 116 in a substantially static position.

As illustrated in FIGS. 1 and 2, a data and control pathway 126, such as a cable or other connection, extends through the handle 102 to the transducer 110. The pathway 126 may extend through a material free region or other channel within the handle 102 to the transducer 110. The other end of the pathway 126 electronically and physically connects to an imaging system console 128 or other computing device.

The imaging system console 128 includes a processor 130 and memory 132. The processor 130 is configured to execute computer executable instructions in the memory 132, including one or more instructions corresponding to a processing algorithm 134 within the memory 132. The processing algorithm 134 may, for example, include one or more instructions for processing image data.

A connection interface 136 routes image data from the ultrasound probe 100 to the console 128. The interface 136 is used to communicate data, control signals and/or other information from the console 128 to the ultrasound probe 100.

An external device port 138 provides a connection of a peripheral device 140 such as, for example, a keyboard, a mouse, or another peripheral device, where a user of the console 128 may input further information or data. Such information and/or data includes a control signal for turning the ultrasound probe 100 on and off, a control signal for initiating transfer of data to and/or from the console 128, and/or a control signal for otherwise controlling the probe 100.

A monitor 142 displays information, including information indicative of the probe 100 within a cavity. Examples of monitor 142 include, but are not limited to, a liquid crystal display (LCD), a seven-segment display, and/or other display.

Variations are contemplated.

In another embodiment, the posterior blade section 104 is detachable from the handle 102 at a proximal fastener. The fastener can be a pin, screw, bolt or other fastener. The posterior section 104 can be detached, which allows for sterilization and/or replacement by one of a plurality of different sections. Sections with varying widths, lengths and/or other shapes can be used where probe 100 is used for different procedures. For example, the probe 100 may be used within a variety of biological cavities, such as, a vagina, an anus, or a throat. The probe 100 may also be used for non-biological cavities, such as, for example, pipes, drains or other cavities.

In another embodiment, the anterior section 112 is longitudinally movable in relation to an axis running substantially parallel to the posterior section 104. Movement occurs towards and/or away from the handle 102, for example, along a slide or otherwise. In this embodiment, the anterior section 112 is fixed into a substantially static position once in a suitable position.

In another embodiment, the anterior section 112 includes a telescoping portion at an end region opposite the handle 102. The telescoping portion increases and/or decreases the length L2 of the anterior section 112. The telescoping movement occurs towards and/or away from the handle 102.

In another embodiment, the transducer 110 is also movable along a longitudinal axis running parallel to the posterior section 104. Movement occurs, for example, along a slide or otherwise. This movement may increase and/or decrease a range of view for the transducer 110. The range of view may be, for example, within a range between 0° and 90°. With the increase and/or decrease of the range of view, varying intensities of ultrasound frequencies may be used. For example, to obtain a suitable image resolution within a region of interest, a frequency within the range of 1 MHz and 20 MHz is used, such as between the range of 5 MHz and 12 MHz.

In another embodiment, the standoffs 114 are a single member, which is received by a single centrally configured recess in handle 102.

In another embodiment, the standoffs 114 include telescoping portions, which telescope away from and/or towards the handle 102.

In another embodiment, the fastener 120 is pulled away from the handle 102 to loosen the standoffs 114 by releasing a latch. The fastener 120 is pushed towards the handle 102 engaging a latch, to lock the standoffs 114 into a substantially static position.

In another embodiment, the fastener 120 is placed into predefined holes located on the handle 102 to alter the position of the standoffs 114.

In another embodiment, the probe 100 includes a wireless communication channel communicating with the console 128. In such an instance, the probe 100 may operate under battery power.

Figure 3:
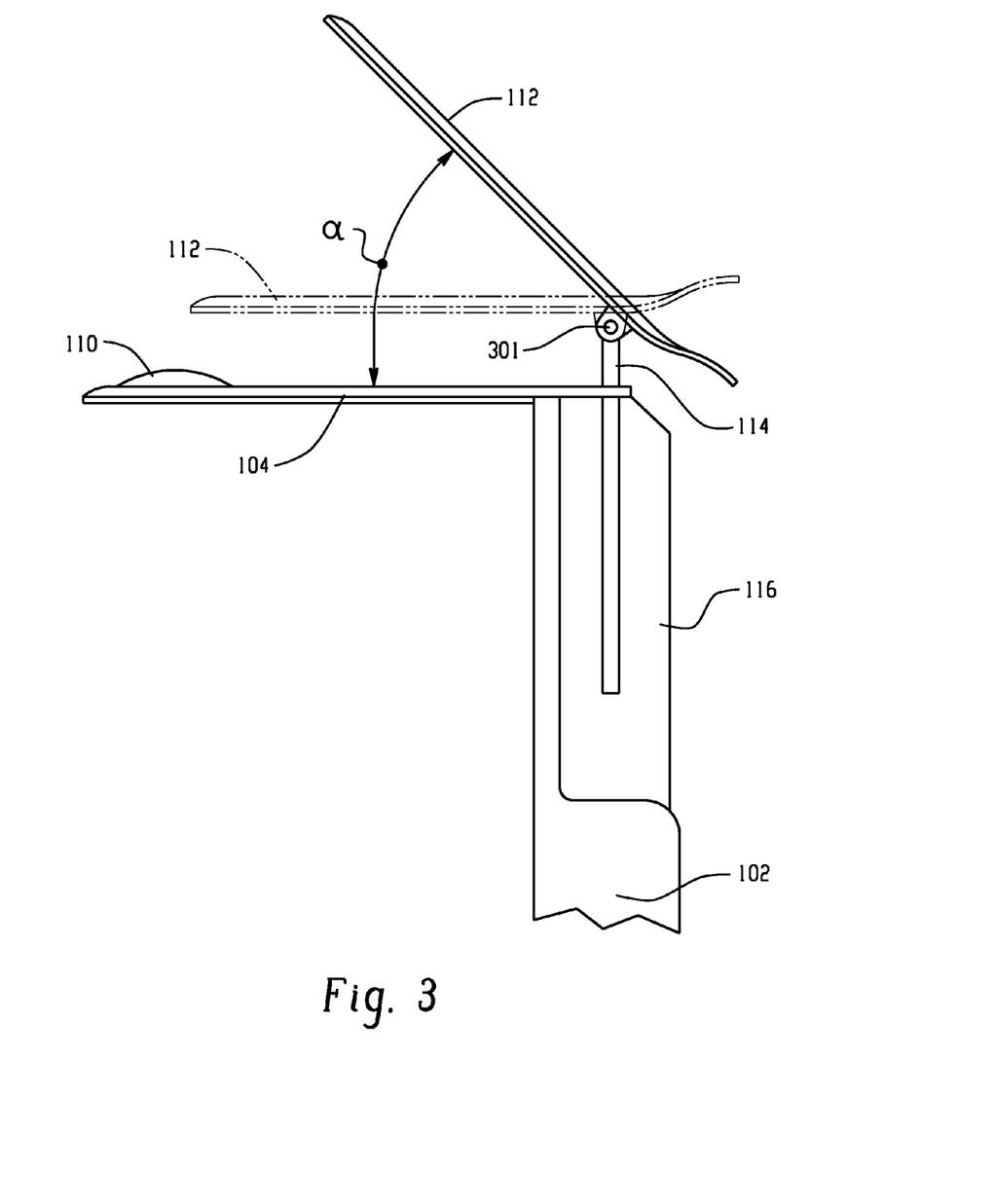
FIG. 3 illustrates a second example probe.

FIG. 3 depicts an embodiment of probe 100 where the anterior blade section 112 is pivotably attached to the handle 102 and pivots through an angle α. The anterior section 112 pivots to change the angle α in relation to the posterior section 104. Movement occurs at a pivot 301, such as pin, hinge or other pivot point. In one instance, the pivot 301 is pushed towards the handle 102 to increase the angle α, for example, within a range between 0° and 180°. In another instance, the pivot point 301 is pushed away from the handle 102 to decrease the angle α.

Figure 4:
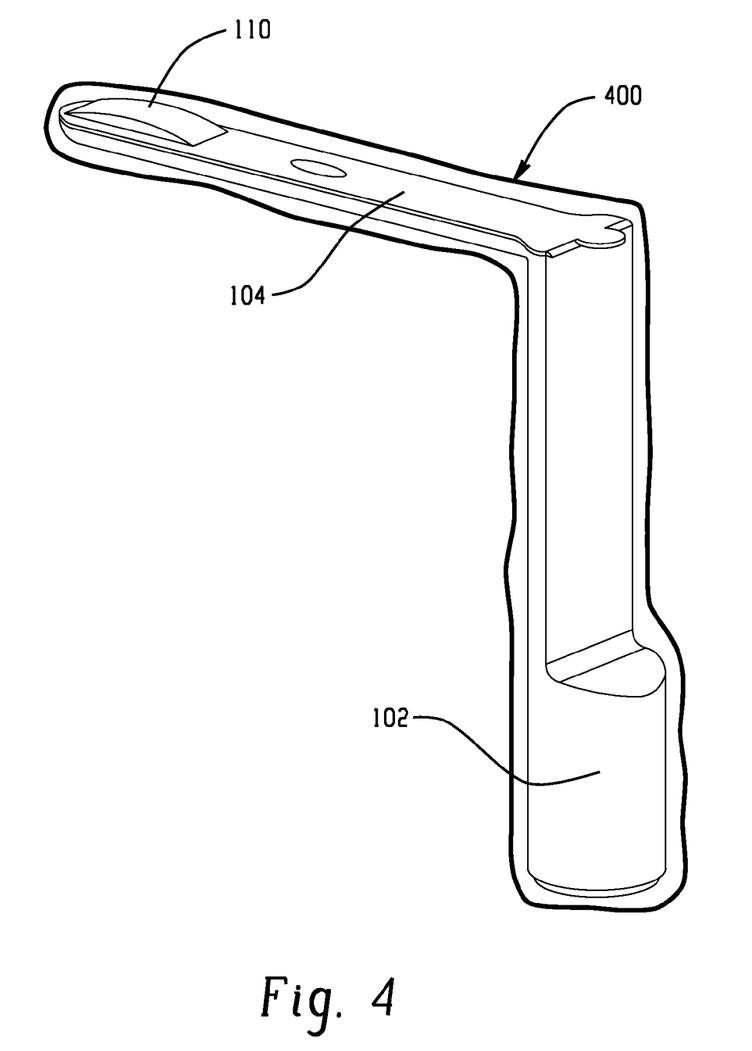
FIG. 4 illustrates the first example probe with a protective cover.

/FIG. 4 depicts a protective covering 400 surrounding the posterior section 104 and the handle 102. In another embodiment, a protective covering 400 is contemplated which covers only the posterior blade section 104 or the handle 102. The protective covering 400 may allow the use of an ultrasound transmitting gel to be used in conjunction with the transducer array 110, increasing the resolution of obtained image data. The protective covering 400 may also provide a barrier through which materials located within a cavity do not contact posterior section 104, alleviating the need for continued sterilization for posterior section 104, thereby extending the useful life of the transducer 110 and/or the posterior section 104.

Figure 5:
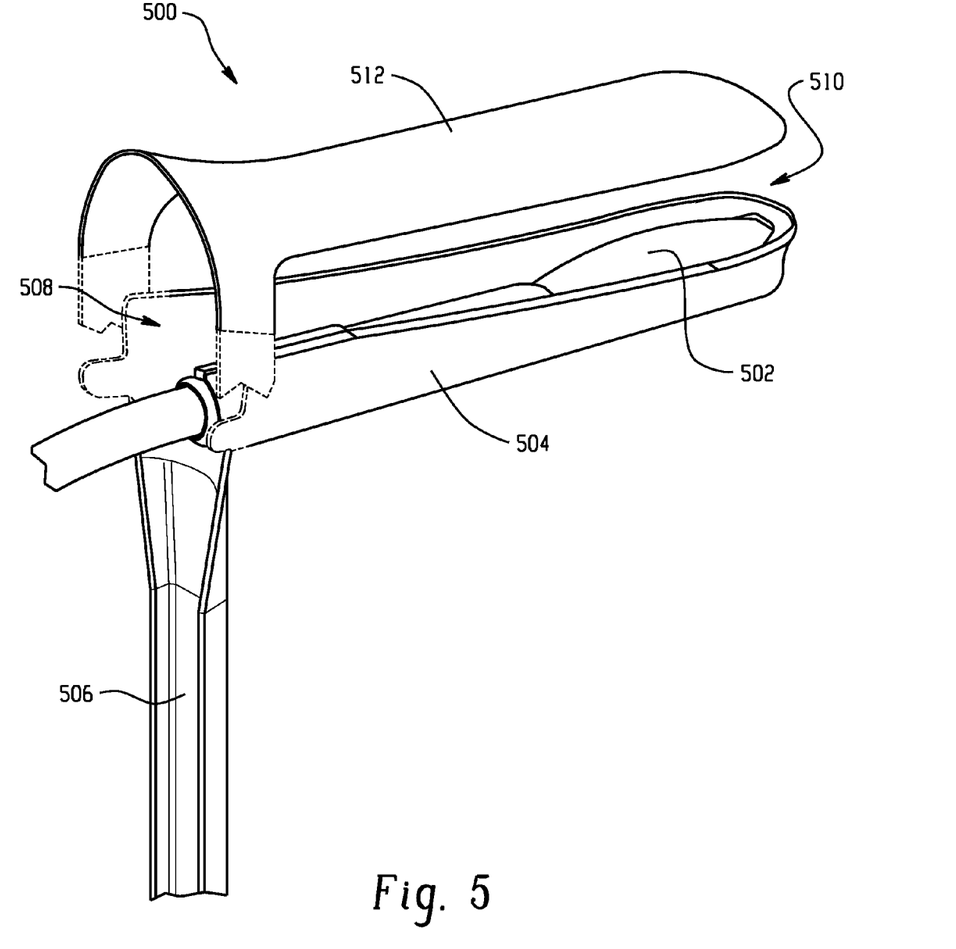
FIG. 5 illustrates a speculum with an attached transducer.

FIG. 5 illustrates an embodiment where an ultrasound transducer 502 is attached to a speculum 500. The transducer 502 is positioned in an upper surface of lower member 504. A speculum 500 for the purposes of this application consists of a hollowed out cylinder attached to a handle 506 with a rounded proximal end 508 and a rounded distal end 510 that is divided into two hinged members 504, 512. The speculum 500 allows direct vision into a cavity and also allows the introduction of instrumentation and/or tools.

Figure 6:
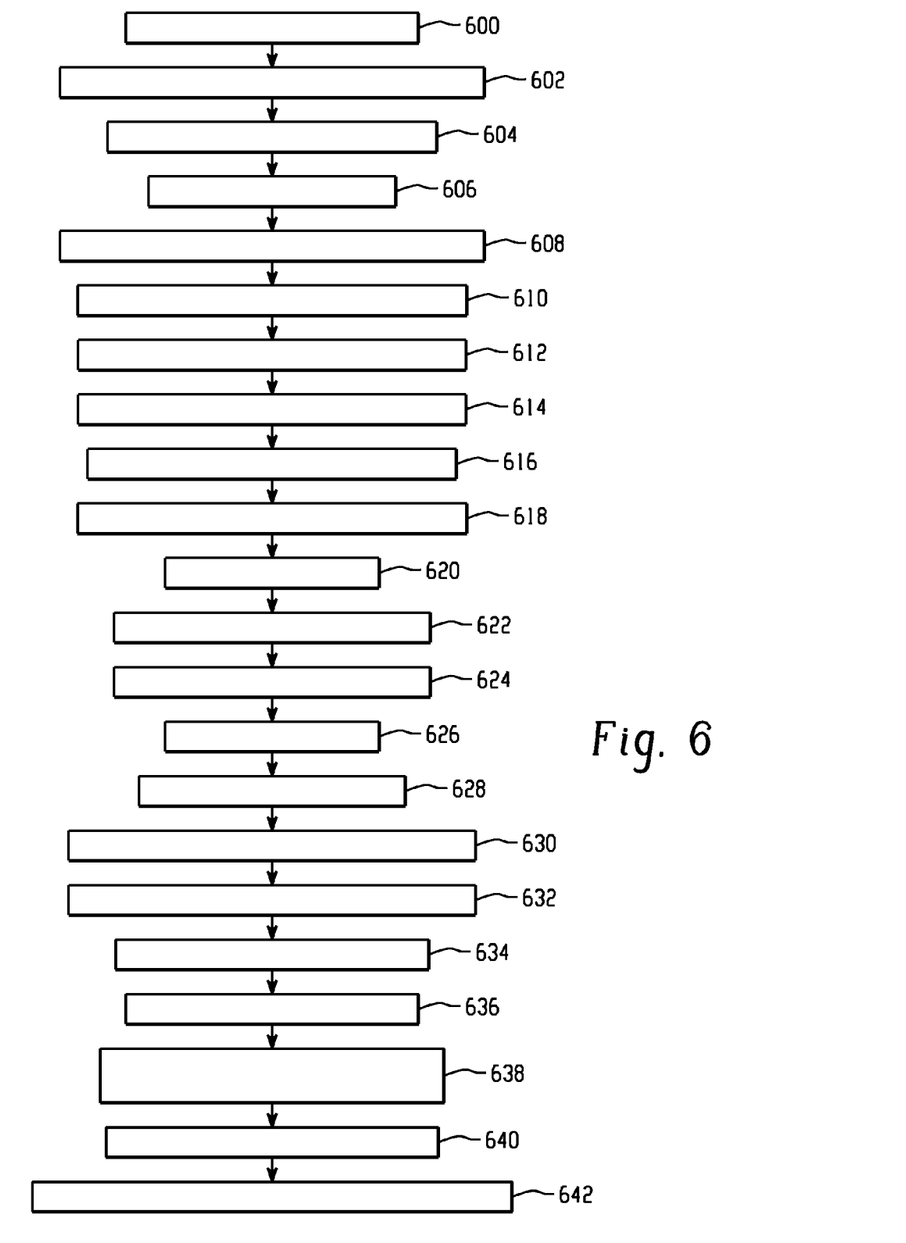
FIG. 6 illustrates an example method. Note the method is in the context of in vitro fertilization, but could be used with another cavity.

FIG. 6 depicts example use of the probe 100 for an in vitro fertilization procedure.

At 600, a suitable anterior section 112 from a plurality of anterior sections 112 is selected. The plurality of anterior sections 112 have varying widths, lengths and/or other shapes.

At 602, the selected anterior section 112 is mounted to the handle attachment 116 and secured by fastener 120 as discussed herein.

At 604, a protective covering 400 is placed around the posterior section 104 and handle 102. In another embodiment, step 604 is omitted.

At 606, the transducer 110 is turned on.

At 608, the handle attachment 116 is mounted to the handle 102. The adjustable bracket 124 holds the handle attachment 116 substantially statically to the handle 102.

At 610, the anterior blade section 112 is moved into a first closed position. As discussed above, the closed position occurs where a surface of the anterior blade section 112 rests upon the surface of the posterior blade 104 in a substantially parallel fashion.

At 612, the probe 100 is inserted into the vaginal canal.

At 614, the position of the transducer 110 is validated using image data obtained from the transducer 110.

At 616, the probe 100 is placed into an open position. This occurs by adjusting the anterior section 112 to a second position, away from the posterior section 104. This positioning can occur manually, electronically or in another manner. In one embodiment, the second position is substantially parallel to an axis running along the posterior blade 104. In another embodiment, the second position is at an angle α from an axis running along the posterior blade 104.

At 618, the position of the transducer 110 is validated while the probe 100 is in the second open position. Any adjustments required due to internal structures and/or movement of the probe 100 while changing positions thereafter occurs.

At 620, a catheter is inserted through the open section of the probe until the end of the catheter reaches into the uterus of the subject patient.

At 622 a suitable location for implantation is determined based on the image data obtained by the transducer 110.

At 624, an embryo is passed via the catheter to the uterus. Images obtained from the transducer 110 are used to determine if the embryo has attached to the uterus of the subject patient.

At 626, the catheter is removed from the vaginal cavity.

At 628, the transducer is turned off.

At 630, the probe 100 is returned to a closed position, with a surface of the anterior section 112 resting upon a surface of the posterior section 104.

At 632, the probe 100 is removed from the vaginal canal.

At 634, the handle attachment 116 is removed from the handle 102 by releasing the adjustable bracket 124.

At 636, the anterior section 112 is removed.

At 638, the anterior section 112 and the handle attachment 116 are sterilized or discarded.

At 640, the protective covering 400 is removed from the posterior section 104 and discarded.

At 642, the posterior section 104 and handle 102 are sterilized.

Steps 600-642 are repeated for a different subject and/or a different procedure, for example, for a new patient, a follow-up examination, or another procedure.

The application has been described with reference to various variations. Modifications and alterations will occur to others upon reading the application. It is intended that the invention be construed as including all such modifications and alterations, including insofar as they come within the scope of the appended claims and the equivalents thereof.

What is claimed is:

1. An ultrasound probe, comprising:
an elongate handle with first and second end regions;
a first blade section attached to the first end region and extending in a direction away from the first end region for a first length (L1), and including a first surface that extends from the first end region for the first length and a second surface opposite the first surface and the second surface extends from the first end region for the first length and the second surface is configured closer to the first end region than first surface relative to a length of the elongated handle;
a second blade section movably attached to the first end region distal to the first blade section relative to the elongated handle and extending in the same direction as the first blade section, wherein the second blade section is configured to move between a first position in which the second blade section is next to the first blade section and a second position in which the second blade section is further away from the first blade section, wherein the second blade section translates away from and towards the first blade section in a plane parallel to the first blade section;
wherein the second surface of the first blade section faces the second blade section and the first surface of the first blade section faces away from the second blade section; and
a transducer array affixed to the first blade section on the second surface opposite the first end region and in between the first and second blade sections, and the transducer array has a view faced by the second surface;
wherein the first blade section extends from the first end region a greater distance than the second blade section extends from the first end region to define a sub-portion of the first blade section, and the transducer array is affixed to and located on the second surface of the first blade section within the sub-portion of the first blade section.

2. The ultrasound probe of claim 1, wherein the second blade section has a second length (L2) relative to the first end region, and the first length (L1) of the first blade section is greater than the second length (L2) of the second blade section; and
wherein the first surface completely encloses surfaces of the first blade section facing away from the second blade section.

3. The ultrasound probe of claim 2, wherein the first length (L1) is greater than the second length (L2) by about 10 mm to 50 mm, and the first length and the second length in a closed position are configured for insertion into a vaginal opening.

4. The ultrasound probe of claim 1, wherein at least one of the first blade section or the second blade section extend from the handle with an angle in a range of about 45° and 135° relative to a latitudinal axis of the handle.

5. The ultrasound probe of claim 4, wherein at least one of the first blade section or the second blade section extend substantially perpendicularly from the handle relative to the latitudinal axis.

6. The ultrasound probe of claim 1, wherein the transducer array emits ultrasound in a frequency range from about 7 MHz to 12 MHz.

7. The ultrasound probe of claim 1, wherein the transducer array is movably affixed to the second surface and configured to move by at least one of: translating along a length of the first blade section or pivoting about the first blade section.

8. The ultrasound probe of claim 1, wherein the transducer array has a field of range of view within a range of about 0° to 360°.

9. The ultrasound probe of claim 1, wherein the second blade section includes standoffs extending from the second blade section in a transverse direction and parallel to the elongated handle; and further comprising:
a handle attachment, affixed to the elongate handle, that includes one or more recesses extending parallel to the elongated handle configured to receive the standoffs, which are moveable in the one or more recesses towards and away from the handle attachment, which moves the second blade section between the first position and the second position.

10. The ultrasound probe of claim 1, further comprising a light source disposed at a central region of the first blade section disposed in between the affixed transducer array and the first end region and within the second surface of the first blade.

11. The ultrasound probe of claim 9, wherein the handle attachment secures the standoffs to the handle, thereby securing the second blade section to the handle.

12. The ultrasound probe of claim 9, the standoffs, further comprising an aperture, and further comprising: a fastener, which engages the aperture, securing the standoffs to the handle.

13. The ultrasound probe of claim 9, further comprising: an adjustable bracket that holds the handle attachment to the handle, and the bracket is pivotally connected to the handle attachment and engages the handle to inhibit movement of the handle attachment in relation to the handle.

14. The ultrasound probe of claim 13, wherein the second blade section and/or the handle attachment are sterilizable.

15. The ultrasound probe of claim 1, wherein the first blade section further comprises a light source located between the transducer array and the first end region, and the light source emits light from the second surface and the light source includes at least one of a laser or a light emitting diode.

16. An ultrasound probe, comprising:
an elongate handle with an end region;
a first blade section protruding from the end region in a direction transverse to the elongate handle for a first length and including a first surface extending from the elongated handle for the first length, and a second surface extending from the elongated handle for the first length and extending laterally to edges of the first blade section and the second surface faces opposite the first surface;
a light source disposed at a central region of the first blade within the second surface, and includes at least one of a laser or a light emitting diode;
a second blade section, which is moveable with respect to the first blade section, wherein the first blade section is longer than the second blade section by an offset and the second blade section faces the second surface; and
a transducer array affixed to the first blade section on the second surface in between the first and second blade sections and within the offset.

17. The ultrasound probe of claim 16, wherein at least one of the first or second blade sections is configured to move towards and away from the other blade section, thereby decreasing or increasing a space therebetween.

18. The ultrasound probe of claim 16, wherein the offset (D4) is within a range of about 20 mm to 30 mm; and wherein a field of view of the transducer array is projected from the second surface.

19. The ultrasound probe of claim 16, wherein the transducer array has a field of range of view, unobstructed by the second blade section in a closed configuration, within a range of about 0° to 360°.

20. The ultrasound probe of claim 16, wherein the second blade section is movably affixed to the probe.

21. The ultrasound probe of claim 16, further comprising: a disposable cover configured to cover at least the first blade section.

22. A method, comprising:
positioning an ultrasound probe within a cavity, the ultrasound probe, comprising:
an elongate handle with first and second end regions;
a first blade section attached to the first end region and extending in a direction away from the first end region, wherein the first blade section has a first length (L1) relative to the first end region and a first surface and a second surface configured closer to the first end region than the first surface relative to a length of the elongated handle, and the first surface and the second surface extend for the first length and the first surface faces away from the second surface;
a second blade section movably attached to the first end region and extending in the same direction as the first blade section, wherein the second blade section has a second length (L2) relative to the first end region and the first length (L1) is greater than the second length (L2) to define an offset, and wherein the second blade section is configured to move towards and away from the first blade section and the second blade section faces the second surface of the first blade section; and
a transducer array affixed to the first blade section opposite to a location at which the first blade section is attached to the handle and in between the first and second blade sections and on the second surface with the offset, and the transducer array has a view faced by the second surface,
wherein the ultrasound probe is not part of a speculum.

* * * * *